US007390519B2

(12) United States Patent
Collins et al.

(10) Patent No.: US 7,390,519 B2
(45) Date of Patent: Jun. 24, 2008

(54) PROBIOTIC *LACTOBACILLUS SALIVARIUS* STRAINS (75) Inventors: John Kevin Collins, Doughcloyne (IE); Gerald Christopher O'Sullivan, Cork (IE); Liam O'Mahony, Cork (IE); Fergus Shanahan, Kinsale (IE); Barry Kiely, Passage West (IE)

(73) Assignee: Alimentary Health Limited (IE)

( * ) Notice: Subject to any disclaimer, the term of this patent is extended or adjusted under 35 U.S.C. 154(b) by 150 days.

(21) Appl. No.: 11/105,590

(22) Filed: Apr. 14, 2005

(65) Prior Publication Data

US 2006/0078547 A1 Apr. 13, 2006

Related U.S. Application Data (63) Continuation of application No. 10/205,318, filed on Jul. 26, 2002, now abandoned.

(30) Foreign Application Priority Data

| Jul. 26, 2001 | (IE) | ................................. 2001/0701 |
| Jul. 26, 2001 | (IE) | ................................. 2001/0702 |
| Jul. 26, 2001 | (IE) | ................................. 2001/0705 |
| Jul. 26, 2001 | (IE) | ................................. 2001/0707 |
| Jul. 26, 2001 | (IE) | ................................. 2001/0708 |

(51) Int. Cl.
*A23L 9/12* (2006.01)
*A61K 35/74* (2006.01)
*C12N 1/20* (2006.01)

(52) U.S. Cl. ..................... 426/61; 424/93.45; 435/252.9
(58) Field of Classification Search ............... 435/252.9; 426/61; 424/93.45
See application file for complete search history.

(56) References Cited

U.S. PATENT DOCUMENTS 6,132,710 A * 10/2000 Panigrahi et al. ......... 424/93.45

FOREIGN PATENT DOCUMENTS

| DE | 19945746 C1 * | 4/2001 |
| JP | 05246864 A * | 9/1993 |
| KR | 2003063960 A * | 7/2003 |
| RU | 2000116 C * | 9/1993 |
| RU | 2055827 C1 * | 3/1996 |
| SU | 1382467 A * | 3/1988 |
| WO | WO98/35014 | 8/1998 |
| WO | WO00/41707 | 7/2000 |

OTHER PUBLICATIONS

Dunne et al, Antonie Van Leeuwenhoek, vol. 76, No. 1-4, Jul. 1999 pp. 279-292, Probiotics: from myth to reality. Demonstration . . . .
O'Mahony et al, Alimentary Pharmacology & Therapeutics, vol. 15, No. 8, Aug. 2001, pp. 1219-1225, Probiotic impact on . . . .
Charteris et al, Jour of Food Protection, vol. 61, No. 12, Dec. 1998, pp. 1636-1643, Antibiotic susceptibility of . . . .
Murphy et al, Microbial Ecology in Health & Disease, vol. 11, 1999, pp. 149-157, In vivo assessment of potential probiotic . . . .
McCracken et al, Probiotics a Critical Review, 1999, pp. 85-113 Probiotics and the Immune System.
Kagnoff, Gastroenterology 105, 1993, pp. 1275-1280, Immunology of the Intestinal Tract.
Lamm, Annu. Rev. Microbiol. 51, 1997, pp. 311-340, Interaction of Antigens and Antibodies at Mucosal Surfaces.
Raychaudhuri et al, Nature Biotechnology, vol. 16, Nov. 1998, pp. 1025-1031, Fully mobilizing host defense: Building . . . .
Stallmach et al, Trends Immunology Today, vol. 19, No. 10, 438, Oct. 1998, Induction and modulation of gatrointestinal . . . .
de Waal Malefyt et al, J. Exp. Med, vol. 174, Oct. 1991, pp. 915-924, Interleukin 10 (IL-10) and Viral IL-10 Strongly . . . .
Schmitt et al, Chem. Immunol. vol. 68, 1997, pp. 70-85, The Immunostimulatory Function of IL-12 in T-Helper Cell . . . .
Leonard et al, Critical Reviews in Immun 17, 1997, pp. 545-553, Regulation of the Inflammatory Response in Animal Models of . . . .
Donnelly et al, Journal of Immun, vol. 145, No. 2, Jul. 15, 1990 pp. 569-575, Differential Regulation of IL-1 Production in . . . .
Wahl et al, Journal of Immun, vol. 146, No. 1, Jan. 1, 1991, pp. 95-100, IFN-γ Inhibits Inflammatory Cell Recruitment and the . . . .
Gatanaga et al, Proc Natl Acad Sci, vol. 87, Nov. 1990, pp. 8781-8784, Purification and characterization of an inhibitor . . . .
Kawakamii et al, Journal of Immun, vol. 132, No. 5, May 1984, pp. 2578-2581, A Group of Bactericidal Factors Conserved . . . .

(Continued)

*Primary Examiner*—Herbert J. Lilling
(74) *Attorney, Agent, or Firm*—Wolf Greenfield & Sacks, P.C.

(57) ABSTRACT

A *Lactobacillus salivarius* strain, AH102, AH103, AH105, AH109 or AH110 or mutants or variants thereof are useful in the prophylaxis and/or treatment of inflammatory activity especially undesirable gastrointestinal inflammatory activity, such as inflammatory bowel disease or irritable bowel syndrome.

20 Claims, 3 Drawing Sheets

OTHER PUBLICATIONS

Mestan et al, Nature, vol. 323, Oct. 30, 1986, pp. 816-819, Antiviral effects of recombinant tumour necrosis factor in vitro.

Ferrante et al, Int Archs Allergy Appl Immun 86, 1988, pp. 82-91, Effects of Tumour Necrosis Factor Alpha and Interleukin-1 . . . .

Bachwich et al, Biochem and Biophys Res Commun, vol. 136, No. 1, Apr. 14, 1986, Tumor Necrosis Factor Stimulates . . . .

Cicco et al, Blood, vol. 75, No. 10, May 15, 1990, pp. 2049-2052, Inducible Production of Interleukin-6 by Human . . . .

Mangan et al, Journal of Immun, vol. 146, No. 5, Mar. 1, 1991, pp. 1541-1546, Lipopolysaccharide, Tumor Necrosis Factor-$\alpha$ . . . .

Dinarello et al, Rev of Infectious Diseases, vol. 10, No. 1, Jan./Feb. 1988, pp. 168-189, New Concepts on the Pathogenesis . . . .

Dekker et al, Chromatographia, vol. 31, No. 11/12, Jun. 1991, pp. 549-553, Sensitive Pulsed Amperometric Detection of Free . . . .

Tagg et al, Bacteriological Rev, vol. 40, No. 3, Sep. 1976. pp. 722-756, Bacteriocins of Gram-Positive Bacteria.

Chauviere et al, Jour of Gen Microbiology 138, 1992, pp. 1689-1696, Adhesion of human *Lactobacillus acidophilus* strain LB . . . .

Crabbe et al, Int Arch Allergy 34, 1968, pp. 362-375, The Normal Microbial Flora as a Major Stimulus for Proliferation . . . .

Henderson et al, Bacteria-Cytokine Interactions in Health, pp. 79-130, Cytokines, homeostasis networks and disease.

Arai et al, Annu Rev Biochem 59, 1990, pp. 783-836, Cytokines: Coordinators of Immune and Inflammatory Responses.

McGee et al, Immunology 86, 1995, pp. 6-11, A synergistic relationship between TNF-$\alpha$, IL-1$\beta$, and TGF-$\beta$1 on IL-$\gamma$ secretion . . . .

Wu et al, Gynecologic Oncology 53, 1994, pp. 59-63, Transfection of Ovarian Cancer Cells with Tumor Necrosis Factor-$\alpha$ . . . .

Rowland, Human Colonic Bacteria: Role in Nutrition . . . , 1995, pp. 155-174, Toxicology of the Colon: Role of the Intestinal . . . .

Walker, Vaccine, vol. 12, No. 5, 1994, pp. 387-400, New strategies for using mucosal vaccination to achieve more . . . .

Steidler et al, Infection and Immunity, vol. 66, No. 7, Jul. 1998, pp. 3183-3189, Mucosal Delivery of Murine . . . .

Medaglini et al, Proc Natl Acad Sci, vol. 92, Jul. 1995, pp. 6868-6872, Mucosal and systemic immune responses to a . . . .

Savage, Microbial Ecology of the Gut, 1977, pp. 277-310, Interactions Between the Host and its Microbes.

* cited by examiner

PROBIOTIC *LACTOBACILLUS SALIVARIUS* STRAINS

This application is a CON of 10/205,318 Jul. 26,2002 ABN, which claims benefit to IRELAND 2001/0708 Jul. 26, 2001; IRELAND 2001/0707 Jul. 26, 2001; IRELAND 2001/0705 Jul. 26, 2001; IRELAND 2001/0702 Jul. 26, 2001; IRELAND 2001/0701 Jul. 26, 2001.

INTRODUCTION

The invention relates to *Lactobacillus salivarius* strains and their use as probiotic bacteria in particular as immunomodulatory biotherapeutic agents.

The defense mechanisms to protect the human gastrointestinal tract from colonization by intestinal bacteria are highly complex and involve both immunological and non-immunological aspects (1). Innate defense mechanisms include the low pH of the stomach, bile salts, peristalsis, mucin layers and anti-microbial compounds such as lysozyme (2). Immunological mechanisms include specialized lymphoid aggregates, underlying M cells, called peyers patches which are distributed throughout the small intestine and colon (3). Luminal antigens presented at these sites result in stimulation of appropriate T and B cell subsets with establishment of cytokine networks and secretion of antibodies into the gastrointestinal tract (4). In addition, antigen presentation may occur via epithelial cells to intraepithelial lymphocytes and to the underlying lamina propria immune cells (5). Therefore, the host invests substantially in immunological defense of the gastrointestinal tract. However, as the gastrointestinal mucosa is the largest surface at which the host interacts with the external environment, specific control mechanisms must be in place to regulate immune responsiveness to the 100 tons of food which is handled by the gastrointestinal tract over an average lifetime. Furthermore, the gut is colonized by over 500 species of bacteria numbering $10^{11}$-$10^{12}$/g in the colon. Thus, these control mechanisms must be capable of distinguishing non-pathogenic adherent bacteria from invasive pathogens, which would cause significant damage to the host. In fact, the intestinal flora contributes to defense of the host by competing with newly ingested potentially pathogenic microorganisms.

Bacteria present in the human gastrointestinal tract can promote inflammation. Aberrant immune responses to the indigenous microflora have been implicated in certain disease states, such as inflammatory bowel disease. Antigens associated with the normal flora usually lead to immunological tolerance and failure to achieve this tolerance is a major mechanism of mucosal inflammation (6). Evidence for this breakdown in tolerance includes an increase in antibody levels directed against the gut flora in patients with IBD.

The present invention is directed towards Lactobacillus strains, which have been shown to have immunomodulatory effects, by modulating cytokine levels or by antagonizing and excluding pro-inflammatory micro-organisms from the gastrointestinal tract.

STATEMENTS OF INVENTION

According to the invention there is provided a Lactobacillus salivarius strain selected from any one or more of AH102, AH103, AH105, AH109 and AH110 or a mutant or variant thereof.

The mutant may be a genetically modified mutant. The variant may be a naturally occurring variant of *Lactobacillus salivarius*.

In one embodiment of the invention *Lactobacillus salivarius* strains are in the form of viable cells. Alternatively *Lactobacillus salivarius* strains are in the form of non-viable cells.

In one embodiment of the invention the strains are in the form of a biologically pure culture.

In one embodiment of the invention the Lactobacillus salivarius strains are isolated from resected and washed human gastrointestinal tract. Preferably the *Lactobacillus salivarius* strains are significantly immunomodulatory following oral consumption in humans.

The invention also provides a formulation which comprises at least one *Lactobacillus salivarius* strain of the invention. The formulation may comprise two or more strains of *Lactobacillus*.

In one embodiment of the invention the formulation includes another probiotic material.

In one embodiment of the invention the formulation includes a prebiotic material.

Preferably the formulation includes an ingestable carrier. The ingestable carrier may be a pharmaceutically acceptable carrier such as a capsule, tablet or powder. Preferably the ingestable carrier is a food product such as acidified milk, yoghurt, frozen yoghurt, milk powder, milk concentrate, cheese spreads, dressings or beverages.

In one embodiment of the invention the formulation of the invention further comprises a protein and/or peptide, in particular proteins and/or peptides that are rich in glutamine/glutamate, a lipid, a carbohydrate, a vitamin, mineral and/or trace element.

In one embodiment of the invention *Lactobacillus salivarius* strains are present in the formulation at more than $10^6$ cfu per gram of delivery system. Preferably the formulation includes any one or more of an adjuvant, a bacterial component, a drug entity or a biological compound.

In one embodiment of the invention the formulation is for immunisation and vaccination protocols.

The invention further provides *Lactobacillus salivarius* strains or a formulation of the invention for use as foodstuffs, as a medicament, for use in the prophylaxis and/or treatment of undesirable inflammatory activity, for use in the prophylaxis and/or treatment of undesirable gastrointestinal inflammatory activity such as inflammatory bowel disease such as Crohns disease or ulcerative colitis, irritable bowel syndrome, pouchitis, or post infection colitis, for use in the prophylaxis and/or treatment of gastrointestinal cancer(s), for use in the prophylaxis and/or treatment of systemic disease such as rheumatoid arthritis, for use in the prophylaxis and/or treatment of autoimmune disorders due to undesirable inflammatory activity, for use in the prophylaxis and/or treatment of cancer due to undesirable inflammatory activity, for use in the prophylaxis of cancer, for use in the prophylaxis and/or treatment of diarrhoeal disease due to undesirable inflammatory activity, such as *Clostridium difficile* associated diarrhoea, Rotavirus associated diarrhoea or post infective diarrhoea, for use in the prophylaxis and/or treatment of diarrhoeal disease due to an infectious agent, such as *E. coli*.

The invention also provides *Lactobacillus salivarius* strains or a formulation of the invention for use in the preparation of an anti-inflammatory biotherapeutic agent for the prophylaxis and/or treatment of undesirable inflammatory activity or for use in the preparation of anti-inflammatory biotherapeutic agents for the prophylaxis and/or treatment of undesirable inflammatory activity.

In one embodiment of the invention the strains of the invention act by antagonising and excluding proinflammatory micro-organisms from the gastrointestinal tract.

The invention also provides *Lactobacillus salivarius* strains or a formulation of the invention for use in the preparation of anti-inflammatory biotherapeutic agents for reducing the levels of pro inflammatory cytokines such as IL8.

The invention further provides *Lactobacillus salivarius* strains for use in the preparation of anti-inflammatory biotherapeutic agents for modulating cytokine levels such as IL-8, IL-10, IL-12, TNFα or IFNγ.

The invention further provides *Lactobacillus salivarius* strains for use in the preparation of biotherapeutic agents for modifying the levels of IFNγ. Preferably in this case the strains are selected from any one of AH102, AH103 or AH105.

The invention further provides *Lactobacillus salivarius* strains for use in the preparation of biotherapeutic agents for modifying the levels of IL-10.

The invention further provides *Lactobacillus salivarius* strains for use in the preparation of biotherapeutic agents for modifying the levels of IL-12.

The invention further provides *Lactobacillus salivarius* strains for use in the preparation of biotherapeutic agents for modifying the levels of IL-8.

The invention further provides Lactobacillus salivarius AH110 for use in the preparation of biotherapeutic agents for modifying the levels of TNFα.

The invention also provides for the use of *Lactobacillus salivarius* strains as anti-infective probiotic strains due to their ability to antagonise the growth of pathogenic species.

We have found that particular strains of *Lactobacillus* elicit immunomodulatory effects in vitro.

The invention is therefore of major potential therapeutic value in the prophylaxis or treatment of dysregulated immune responses, such as undesirable inflammatory reactions, for example inflammatory bowel disease.

The strains may be used as a panel of biotherapeutic agents from which a selection can be made for modifying the levels of IFNγ, TNFα, IL-8, IL-10 and/or IL-12.

The strains or formulations of the invention may be used in the prevention and/or treatment of inflammatory disorders, immunodeficiency, inflammatory bowel disease, irritable bowel syndrome, cancer (particularly of the gastrointestinal and immune systems), diarrhoeal disease, antibiotic associated diarrhoea, paediatric diarrhoea, appendicitis, autoimmune disorders, multiple sclerosis, Alzheimer's disease, rheumatoid arthritis, coeliac disease, diabetes mellitus, organ transplantation, bacterial infections, viral infections, fungal infections, periodontal disease, urogenital disease, sexually transmitted disease, HIV infection, HIV replication, HIV associated diarrhoea, surgical associated trauma, surgical-induced metastatic disease, sepsis, weight loss, anorexia, fever control, cachexia, wound healing, ulcers, gut barrier function, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, epidermal disorders, psoriasis and/or acne vulgaris.

The *Lactobacillus* strains are commensal microorganisms. They have been isolated from the microbial flora within the human gastrointestinal tract. The immune system within the gastrointestinal tract cannot have a pronounced reaction to members of this flora, as the resulting inflammatory activity would also destroy host cells and tissue function.

Therefore, some mechanism(s) exist whereby the immune system can recognize commensal non-pathogenic members of the gastrointestinal flora as being different to pathogenic organisms. This ensures that damage to host tissues is restricted and a defensive barrier is still maintained.

A deposit of *Lactobacillus salivarius* strain AH102 was made at the National Collections of Industrial and Marine Bacteria Limited (NCIMB) on Apr. 20, 2000 and accorded the accession number NCIMB 41044.

A deposit of *Lactobacillus salivarius* strain AH103 was made at the NCIMB on Apr. 20, 2000 and accorded the accession number NCIMB 41045.

A deposit of *Lactobacillus salivarius* strain AH105 was made at the NCIMB on Apr. 20, 2000 and accorded the accession number NCIMB 41047.

A deposit of *Lactobacillus salivarius* strain AH109 was made at the NCIMB on Mar. 22, 2001 and accorded the accession number NCIMB 41093.

A deposit of *Lactobacillus salivarius* strain AH110 was made at the NCIMB on Mar. 22, 2001 and accorded the accession number NCIMB 41094.

The *Lactobacillus salivarius* may be a genetically modified mutant or it may be a naturally occurring variant thereof.

Preferably the *Lactobacillus salivarius* is in the form of viable cells. Alternatively the *Lactobacillus salivarius* may be in the form of non-viable cells.

It will be appreciated that the specific *Lactobacillus* strain of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives. The amount of active ingredient in the medical composition may be at a level that will exercise the desired therapeutic effect.

The formulation may also include a bacterial component, a drug entity or a biological compound.

In addition a vaccine comprising any one or more of the strains of the invention may be prepared using any suitable known method and may include a pharmaceutically acceptable carrier or adjuvant.

Throughout the specification the terms mutant, variant and genetically modified mutant include a strain of Lactobacillus salivarius whose genetic and/or phenotypic properties are altered compared to the parent strain. Naturally occurring variant of *Lactobacillus salivarius* includes the spontaneous alterations of targeted properties selectively isolated while deliberate alteration of parent strain properties may be accomplished by conventional genetic manipulation technologies, such as gene disruption, conjugative transfer, etc.

DETAILED DESCRIPTION

We have found that Lactobacillus salivarius strains AH102, AH103, AH105, AH109 and AH110 are not only acid and bile tolerant and adhere to human intestinal cell lines but also, surprisingly have immunomodulatory effects, by modulating cytokine levels or by antagonising and excluding pro-inflammatory or immunomodulatory micro-organisms from the gastrointestinal tract.

The general use of probiotic bacteria is in the form of viable cells. However, it can also be extended to non-viable cells such as killed cultures or compositions containing beneficial factors expressed by the probiotic bacteria. This could include thermally killed micro-organisms or micro-organisms killed by exposure to altered pH or subjection to pressure. With non-viable cells product preparation is simpler, cells may be incorporated easily into pharmaceuticals and storage requirements are much less limited than viable cells. *Lactobacillus casei* YIT 9018 offers an example of the effective use of heat killed cells as a method for the treatment and/or prevention of tumour growth as described in U.S. Pat. No. 4,347,240.

It is unknown whether intact bacteria are required to exert an immunomodulatory effect or if individual active components of the invention can be utilized alone. Proinflammatory components of certain bacterial strains have been identified. The proinflammatory effects of gram-negative bacteria are mediated by lipopolysaccharide (LPS). LPS alone induces a proinflammatory network, partially due to LPS binding to the CD14 receptor on monocytes. It is assumed that components of probiotic bacteria possess immunomodulatory activity, due to the effects of the whole cell. Upon isolation of these components, pharmaceutical grade manipulation is anticipated.

Interleukin-8 (IL-8) is one of the cytokines comprising the Macrophage Inflammatory protein family (MIP). The MIP-1 and -2 families represent a group of proteins which are chemotactic factors for leukocytes and fibroblasts. This family of proteins are also called intercrines, as cells other than macrophages are capable of synthesizing them. These cells include T and B cells, fibroblasts, endothelial cells, keratinocytes, smooth muscle cells, synovial cells, neutrophils, chondrocytes, hepatocytes, platelets and tumour cells. MIP-1α, -1β, connective tissue activating protein (CTAP), platelet factor 4 (PF4) and IL-8 stimulate neutrophil chemotaxis. Monocyte chemotactic protein (MCP-1) and RANTES are chemotactic for monocytes, IL-8 for neutrophils and lymphocytes while PF4 and CTAP are chemotactic for fibroblasts. Roles other than chemotaxis have been described for some of these family members. MCP-1 stimulates monocyte cytostatic activity and superoxide anion release. CTAP and PF4 increase fibroblast proliferation, IL-8 increases vascular permeability while MIP-1α and -1β are pyrogenic. IL-8 is intimately involved in inflammatory responses within the gastrointestinal tract. Stimulation of IL-8 (and other proinflammatory cytokines) could contribute to the development of gastrointestinal lesions therefore it is important that probiotic bacteria should not stimulate the production of this cytokine.

IL-10 is produced by T cells, B cells, monocytes and macrophages. This cytokine augments the proliferation and differentiation of B cells into antibody secreting cells. IL-10 exhibits mostly anti-inflammatory activities. It up-regulates IL-1RA expression by monocytes and suppresses the majority of monocyte inflammatory activities. IL-10 inhibits monocyte production of cytokines, reactive oxygen and nitrogen intermediates, MHC class II expression, parasite killing and IL-10 production via a feed back mechanism (7). This cytokine has also been shown to block monocyte production of intestinal collagenase and type IV collagenase by interfering with a $PGE_2$-cAMP dependant pathway and therefore may be an important regulator of the connective tissue destruction seen in chronic inflammatory diseases.

IL-12 is a heterodimeric protein of 70 kD composed of two covalently linked chains of 35 kD and 40 kD. It is produced primarily by antigen presenting cells, such as macrophages, early in the inflammatory cascade. Intracellular bacteria stimulate the production of high levels of IL-12. It is a potent inducer of IFNγ production and activator of natural killer cells. IL-12 is one of the key cytokines necessary for the generation of cell mediated, or Th1, immune responses primarily through its ability to prime cells for high IFNγ production (8). IL-12 induces the production of IL-10 which feedback inhibits IL-12 production thus restricting uncontrolled cytokine production. TGF-β also down-regulates IL-12 production. IL-4 and IL-13 can have stimulatory or inhibitory effects on IL-12 production. Inhibition of IL-12 in vivo may have some therapeutic value in the treatment of Th1 associated inflammatory disorders, such as multiple sclerosis (9).

Interferon-gamma (IFNγ) is primarily a product of activated T lymphocytes and due to variable glycosylation it can be found ranging from 20 to 25 kDa in size. This cytokine synergizes with other cytokines resulting in a more potent stimulation of monocytes, macrophages, neutrophils and endothelial cells. IFNγ also amplifies lipopolysaccharide (LPS) induction of monocytes and macrophages by increasing cytokine production (10), increased reactive intermediate release, phagocytosis and cytotoxicity. IFNγ induces, or enhances the expression of major histocompatibility complex class II (MHC class II) antigens on monocytic cells and cells of epithelial, endothelial and connective tissue origin. This allows for greater presentation of antigen to the immune system from cells within inflamed tissues. IFNγ may also have anti-inflammatory effects. This cytokine inhibits phospholipase $A_2$, thereby decreasing monocyte production of $PGE_2$ and collagenase (11). IFNγ may also modulate monocyte and macrophage receptor expression for TGFβ, TNFα and C5a (11) thereby contributing to the anti-inflammatory nature of this cytokine. Probiotic stimulation of this cytokine would have variable effects in vivo depending on the current inflammatory state of the host, stimulation of other cytokines and the route of administration.

TNFα is a proinflammatory cytokine which mediates many of the local and systemic effects seen during an inflammatory response. This cytokine is primarily a monocyte or macrophage derived product but other cell types including lymphocytes, neutrophils, NK cells, mast cells, astrocytes, epithelial cells endothelial cells and smooth muscle cells can also synthesise TNFα. TNFα is synthesised as a prohormone and following processing the mature 17.5 kDa species can be observed. Purified TNFα has been observed as dimers, trimers and pentamers with the trimeric form postulated to be the active form in vivo. Three receptors have been identified for TNFα. A soluble receptor seems to function as a TNFα inhibitor (12) while two membrane bound forms have been identified with molecular sizes of 60 and 80 kDa respectively. Local TNFα production at inflammatory sites can be induced with endotoxin and the glucocorticoid dexamethasone inhibits cytokine production (13). TNFα production results in the stimulation of many cell types. Significant anti-viral effects could be observed in TNFα treated cell lines (14) and the IFNs synergise with TNFα enhancing this effect. Endothelial cells are stimulated to produce procoagulant activity, expression of adhesion molecules, IL-1, hematopoitic growth factors, platelet activating factor (PAF) and arachidonic acid metabolites. TNFα stimulates neutrophil adherence, phagocytosis, degranulation (15), reactive oxygen intermediate production and may influence cellular migration. Leucocyte synthesis of GM-CSF, TGFβ, IL-1, IL-6, PGE2 and TNFα itself can all be stimulated upon TNFα administration (16, 17). Programmed cell death (apoptosis) can be delayed in monocytes (18) while effects on fibroblasts include the promotion of chemotaxis and IL-6, $PGE_2$ and collagenase synthesis. While local TNFα production promotes wound healing and immune responses, the dis-regulated systemic release of TNFα can be severely toxic with effects such as cachexia, fever and acute phase protein production being observed (19).

The invention will be more clearly understood from the following examples.

EXAMPLE 1

Characterisation of Bacteria Isolated from Resected and Washed Human Gastrointestinal Tract. Demonstration of Probiotic Traits Isolation of Probiotic Bacteria Appendices and sections of the large and small intestine of the human gastrointestinal tract (G.I.T.) obtained during reconstructive surgery, were screened for probiotic bacterial strains. All samples were stored immediately after surgery at −80° C. in sterile containers.

Frozen tissues were thawed, weighed and placed in cysteinated (0.05%) one quarter strength Ringers' solution. The sample was gently shaken to remove loosely adhering microorganisms (termed—wash 'W'). Following transfer to a second volume of Ringer's solution, the sample was vortexed for 7 mins to remove tightly adhering bacteria (termed—sample 'S'). In order to isolate tissue embedded bacteria, samples 356, 176 and A were also homogenized in a Braun blender (termed—homogenate 'H'). The solutions were serially diluted and spread-plated (100 µl) on the following agar media: RCM (reinforced clostridia media) and RCM adjusted to pH 5.5 using acetic acid; TPY (trypticase, peptone and yeast extract); MRS (deMann, Rogosa and Sharpe); ROG (acetate medium (SL) of Rogosa); LLA (liver-lactose agar of Lapiere); BHI (brain heart infusion agar); LBS (*Lactobacillus* selective agar) and TSAYE (tryptone soya sugar supplemented with 0.6% yeast extract). TPY and MRS supplemented with propionic acid was also used. All agar media was supplied by Oxoid Chemicals with the exception of TPY agar. Plates were incubated in anaerobic jars (BBL, Oxoid) using $CO_2$ generating kits (Anaerocult A, Merck) for 2-5 days at 37° C.

Gram positive, catalase negative rod-shaped or bifurcated/pleomorphic bacteria isolates were streaked for purity on to complex non-selective media (MRS and TPY). Isolates were routinely cultivated in MRS or TPY medium unless otherwise stated at 37° C. under anaerobic conditions. Presumptive *Lactobacillus* were stocked in 40% glycerol and stored at −20° C. and −80° C.

Seven tissue sections taken from the G.I.T. were screened for the presence of strains belonging to the *Lactobacillus* genera. There was some variation between tissue samples. Table 1 below shows the bacterial count of the tissue samples expressed as colony forming units per gram (cfu/ml) of tissue. (nd=not determined)

TABLE 1

| Isolation Medium | Tissue Sample No. | | | | | | |
|---|---|---|---|---|---|---|---|
| | A | 176 | 356 | 312 | 316 | 423 | 433 |
| 'WASH' Solution | | | | | | | |
| MRS | $57 \times 10^2$ | $>9.0 \times 10^3$ | $3.3 \times 10^3$ | $>3.0 \times 10^4$ | 0 | $3.2 \times 10^3$ | $8.0 \times 10^2$ |
| TPYP | 0 | $>9.0 \times 10^3$ | $>6.0 \times 10^3$ | $>3.0 \times 10^4$ | 0 | $1.9 \times 10^2$ | $2.8 \times 10^2$ |
| RCM5.5 | 0 | 0 | $3.1 \times 10^2$ | $1.8 \times 10^4$ | ND | $3.0 \times 10^1$ | $8.0 \times 10^2$ |
| ROG | 0 | $>9.0 \times 10^3$ | $>6.0 \times 10^3$ | $7.7 \times 10^2$ | $3.8 \times 10^2$ | $9.7 \times 10^1$ | $4.0 \times 10^1$ |
| TSAYE | $3.9 \times 10^2$ | $>9.0 \times 10^3$ | $>6.0 \times 10^3$ | ND | ND | ND | ND |
| LLA | $2.5 \times 10^2$ | $>9.0 \times 10^3$ | $>6.0 \times 10^3$ | ND | $5.3 \times 10^2$ | ND | ND |
| RCM | ND | ND | ND | $>3.0 \times 10^4$ | ND | $4.8 \times 10^3$ | $4.6 \times 10^3$ |
| 'SAMPLE' Solution | | | | | | | |
| MRS | $1.35 \times 10^3$ | $>9.0 \times 10^3$ | $>6.0 \times 10^3$ | $1.66 \times 10^4$ | $2.3 \times 10^2$ | $>1.0 \times 10^4$ | $9.6 \times 10^2$ |
| TPYP | 0 | $>9.0 \times 10^3$ | $>6.0 \times 10^3$ | $>3.0 \times 10^4$ | $4.6 \times 10^2$ | 0 | $8.0 \times 10^3$ |
| RCM5.5 | 0 | $>9.0 \times 10^3$ | $>6.0 \times 10^3$ | $1.7 \times 10^3$ | ND | $1.1 \times 10^3$ | $1.5 \times 10^3$ |
| ROG | $1.37 \times 10^2$ | $>9.0 \times 10^3$ | $>6.0 \times 10^3$ | $4.4 \times 10^2$ | $4.5 \times 10^3$ | $1.7 \times 10^3$ | $6.1 \times 10^3$ |
| TSAYE | $1.4 \times 10^3$ | $>9.0 \times 10^3$ | ND | ND | ND | ND | ND |
| LLA | $6.3 \times 10^2$ | $>9.0 \times 10^3$ | $>6.0 \times 10^3$ | ND | $3.0 \times 10^2$ | ND | ND |
| RCM | ND | ND | ND | $>3.0 \times 10^4$ | ND | $>1.0 \times 10^4$ | ND |
| 'HOMOGENATE' Solution | | | | | | | |
| MRS | 0 | 0 | $>6.0 \times 10^3$ | | | | |
| TPYP | 0 | 0 | $>6.0 \times 10^3$ | | | | |
| RCM5.5 | 0 | 0 | $2.5 \times 10^2$ | | | | |
| ROG | 0 | 0 | $>6.0 \times 10^3$ | | | | |
| TSAYE | $3.9 \times 10^1$ | 0 | $>6.0 \times 10^3$ | | | | |
| LLA | $1.9 \times 10^1$ | $6.57 \times 10^2$ | $>6.0 \times 10^3$ | | | | |
| RCM | 0 | 0 | ND | | | | |

Samples A (ileum) and 316 (appendix) had the lowest counts with approximately $10^2$ cells isolated per gram of tissue. In comparison, greater $10^3$ cfu/g tissue were recovered from the other samples. Similar numbers of bacteria were isolated during the 'wash' and 'sample' steps with slightly higher counts in the 'sample' solutions of 433 (ileal-caecal).

Fermentation and Growth Characteristics

Metabolism of the carbohydrate glucose and the subsequent organic acid end-products were examined using an LKB Bromma, Aminex HPX-87H High Performance Liquid Chromatography column. The column was maintained at 60° C. with a flow rate of 0.6 ml/min (constant pressure). The HPLC buffer used was 0.01 N $H_2SO_4$. Prior to analysis, the column was calibrated using 10 mM citrate, 10 mM glucose, 20 mM lactate and 10 mM acetate as standards. Cultures were propagated in modified MRS broth for 1-2 days at 37° C. anaerobically. Following centrifugation for 10 min at 14,000 g, the supernatant was diluted 1:5 with HPLC buffer and 200 μl was analysed in the HPLC. All supernatants were analysed in duplicate.

Biochemical and physiological traits of the bacterial isolates were determined to aid identification. Nitrate reduction, indole formation and expression of β-galactosidase activity were assayed. Growth at both 15° C. and 45° C., growth in the presence of increasing concentrations of NaCl up to 5.0% and protease activity on gelatin were determined. Growth characteristics of the strains in litmus milk were also assessed.

Approximately fifteen hundred catalase negative bacterial isolates from different samples were chosen and characterised in terms of their Gram reaction, cell size and morphology, growth at 15° C. and 45° C. and fermentation end-products from glucose (data not shown). Greater than sixty percent of the isolates tested were Gram positive, homofermentative cocci (HOMO-) arranged either in tetrads, chains or bunches. Eighteen percent of the isolates were Gram negative rods and heterofermentative coccobacilli (HETERO-). The remaining isolates (twenty two percent) were predominantly homofermentative coccobacilli. Thirty eight strains were characterised in more detail—13 isolates from 433; 4 from 423; 8 from 312; 9 from 356; 3 from 176 and 1 from 316. All thirty eight isolates tested negative both for nitrate reduction and production of indole from tryptophan. Growth at different temperatures, concentrations of NaCl and gelatin hydrolysis are recorded in Table 2 below.

pension medium provided with the kit. API strips were inoculated and analysed (after 24 and 48 h) according to the manufacturers' instructions. Identity of the *Lactobacillus* sp. was then checked by SDS-Polyacrylamide gel electrophoresis analysis (SDS-PAGE) of total cell protein (Bruno Pot, University of Ghent, Belgium, personal communication). Finally, 16s RNA analysis and ribotyping were used to confirm strain identity.

The API 50CHL allowed rapid identification of the *Lactobacillus* isolates. Analysis of total cell protein of the *Lactobacillus* sp. (Bruno Pot, personal communication) by SDS-PAGE, 16s RNA analysis and ribotyping revealed further information on the specific species. Table 3 below shows the identification of the 5 *Lactobacillus* strains by four different techniques.

TABLE 3

| Strain | Sugar fermentation profiles | Total cell protein (SDS-PAGE)* | 16s RNA identification | Ribotyping |
|---|---|---|---|---|
| AH102 | L. salivarius | L. salivarius subsp. salivarius | L. salivarius | L. salivarius subsp. salicinius |
| AH103 | L. salivarius | L. salivarius subsp. salivarius | L. salivarius | L. salivarius subsp. salicinius |
| AH105 | L. salivarius | L. paracasei subsp. paracasei | L. salivarius | L. salivarius |
| AH109 | L. salivarius | L. salivarius subsp. salivarius | L. salivarius | L. salivarius subsp. salicinius |
| AH110 | L. salivarius | L. salivarius subsp. salivarius | L. salivarius | L. salivarius subsp. salicinius |

Enzyme Activity Profiles

The API ZYM system (BioMerieux, France) was used for semi-quantitative measurement of constitutive enzymes pro-

TABLE 2

| Strain | Source | Fermentation Pattern | Temperature Profiles | | % NaCl* | Gelatin Hydrolysis | Reactions in litmus milk | |
|---|---|---|---|---|---|---|---|---|
| | | | 15° C. | 45° C. | | | pH** | RED$^n$ |
| AH102 | S1 ROG | HOMO- | +(s) | – | 3.0 | – | 6.3 | NR |
| AH103 | S1 RCM5.5 | HETERO- | – | – | 3.0 | – | 5.2 | RpCp |
| AH105 | S1 MRSP | HOMO- | – | – | 0.8 | – | 4.9 | RpCp |
| AH109 | S1 TPY | HOMO- | – | – | 5.0 | – | 6.0 | NR |
| AH110 | S1 ROG | HOMO- | – | – | 5.0 | – | 4.9 | RpCp |

HOMO-, homofermentative;
HETERO-, heterofermentative;
–, Negative for reaction/growth;
+, Positive reaction/growth;
+(s), slow growth;
REDn, Reduction;
NR, no reaction;
Rp, Partial reduction;
Cp, Partial clotting;
*Maximum concentration of NaCl in which the strain will grow
**pH after 24 h incubation in litmus milk at 37° C.

Species Identification

The API 50CHL (BioMerieux SA, France) system was used to tentatively identify the *Lactobacillus* species by their carbohydrate fermentation profiles. Overnight MRS cultures were harvested by centrifugation and resuspended in the susduced by *Lactobacillus* isolates. Bacterial cells from the late logarithmic growth phase were harvested by centrifugation at 14,000 g for 10 mins. The pelleted cells were washed and resuspended in 50 mM phosphate buffer, pH 6.8 to the same optical density. The strips were inoculated in accordance with the manufacturer's instructions, incubated for 4 h at 37° C. and colour development recorded.

The enzyme activity profiles of the 5 strains AH102, AH103, AH105, AH 109, AH110 are presented in Table 4 below. None of the strains exhibited lipase, trypsin, α-chymotrypsin, α-glucuronidase, α-mannosidase or α-fucosidase activities.

TABLE 4

|  | AH102 | AH103 | AH105 | AH109 | AH110 |
|---|---|---|---|---|---|
| Alkaline Phosphate | 3 | 3 | 4 | 3 | 3 |
| Esterase | 1 | 1 | 1 | 1 | 1 |
| Esterase Lipase | 1 | 1 | 1 | 1 | 1 |
| Lipase | 0 | 0 | 0 | 0 | 0 |
| Leucine Arylamidase | 4 | 3 | 4 | 3 | 3 |
| Valine Arylamidase | 0 | 1 | 1 | 1 | 1 |
| Cystine Arlyamidase | 5 | 5 | 4 | 4 | 5 |
| Trypsin | 0 | 0 | 0 | 0 | 0 |
| α-Chymotrypsin | 0 | 0 | 0 | 0 | 0 |
| Phosphate acid | 5 | 5 | 5 | 5 | 5 |
| Phosphohydrolase | 5 | 5 | 4 | 4 | 5 |
| α-Galactosidase | 0 | 3 | 4 | 3 | 3 |
| β-Galactosidase | 3 | 4 | 4 | 5 | 4 |
| β-glucuronidase | 0 | 0 | 0 | 0 | 0 |
| α-Glucosidase | 0 | 0 | 0 | 0 | 0 |
| β-Glucosidase | 0 | 0 | 0 | 0 | 0 |
| α-Glucosaminidase | 0 | 0 | 0 | 0 | 0 |
| α-Mannosidase | 0 | 0 | 0 | 0 | 0 |
| α-Fucosidase | 0 | 0 | 0 | 0 | 0 |

Antibiotic Sensitivity Profiles

Antibiotic sensitivity profiles of the isolates were determined using the 'disc susceptibility' assay. Cultures were grown up in the appropriate broth medium for 24-48 h spread-plated (100 µl) onto agar media and discs containing known concentrations of the antibiotics were placed onto the agar. Strains were examined for antibiotic sensitivity after 1-2 days incubation at 37° C. under anaerobic conditions. Strains were considered sensitive if zones of inhibition of 1 mm or greater were seen.

Antibiotics of human clinical importance were used to ascertain the sensitivity profiles of each of the 5 *Lactobacillus* strains. Each of the lactobacilli tested was sensitive to ampicillin, amoxacillin, ceftaxime, ceftriaxone, ciprofloxacin, cephradine, rifampicin and chloramphenicol. The antibiotic sensitivities (ug/ml) of *Lactobacillus salivarius* AH102, AH103, AH105, AH109 and AH110 are given in Table 5 below.

TABLE 5

|  | AH102 | AH103 | AH105 | AH109 | AH110 |
|---|---|---|---|---|---|
| NET 10 | R | R | R | R | S |
| AMP 25 | S | S | S | S | S |
| AMC 30 | S | S | S | S | S |
| AK 30 | R | R | R | R | S |
| W 1.25 | R | R | R | R | R |
| TEC 30 | R | S | S | R | R |
| CXM 30 | S | S | S | S | S |
| CTX 30 | S | S | S | S | S |
| ZOX 30 | S | S | S | S | R |
| CRO 30 | S | S | S | S | S |
| CIP 5 | S | S | S | S | S |
| CN 10 | R | R | R | R | S |
| MTZ 5 | R | R | R | R | R |
| CE 30 | S | S | S | S | S |
| RD 5 | S | S | S | S | S |
| V 5 | R | ND | S | R | R |
| C 10 | S | ND | S | S | S |
| TE 10 | S | ND | S | S | S |

TABLE 5-continued

|  | AH102 | AH103 | AH105 | AH109 | AH110 |
|---|---|---|---|---|---|
| E 5 | S | ND | S | S | S |
| NA 30 | R | R | R | R | R |

R, resistant;
S, sensitive;
ND, not determined

Growth of Lactobacilli at Low pH

Human gastric juice was obtained from healthy subjects by aspiration through a nasogastric tube (Mercy Hospital, Cork, Ireland). It was immediately centrifuged at 13,000 g for 30 min to remove all solid particles, sterilised through 0.45 µm and 0.2 µm filters and divided into 40 ml aliquots which were stored at 4° C. and −20° C.

The pH and pepsin activity of the samples were measured prior to experimental use. Pepsin activity was measured using the quantitative haemoglobulin assay. Briefly, aliquots of gastric juice (1 ml) were added to 5 ml of substrate (0.7 M urea, 0.4% (w/v) bovine haemoglobulin (Sigma Chemical Co., 0.25 M KCl-HCl buffer, pH 2.0) and incubated at 25° C. Samples were removed at 0, 2, 4, 6, 8, 10, 20 and 30 min intervals. Reactions were terminated by the addition of 5% trichloracetic acid (TCA) and allowed to stand for 30 min without agitation. Assay mixtures were then filtered (Whatman, no. 113), centrifuged at 14,000 g for 15 min and absorbance at 280 nm was measured. One unit of pepsin enzyme activity was defined as the amount of enzyme required to cause an increase of 0.001 units of $A_{280}$ nm per minute at pH 2.0 measured as TCA-soluble products using haemoglobulin as substrate.

To determine whether growth of the Lactobacillus strains occurred at low pH values equivalent to those found in the stomach, overnight cultures were inoculated (1%) into fresh MRS broth adjusted to pH4.0, 3.0, 2.0 and 1.0 using 1N HCl. At regular intervals aliquots (1.5 ml) were removed, optical density at 600 nm (OD600) was measured and colony forming units per ml (cfu/ml) calculated using the plate count method. Growth was monitored over a 24-48 h period.

Survival of the strains at low pH in vitro was investigated using two assays:

(a) Cells were harvested from fresh overnight cultures, washed twice in phosphate buffer (pH 6.5) and resuspended in MRS broth adjusted to pH 3.5, 3.0, 2.5, and 2.0 (with 1N HCl) to a final concentration of approximately $10^8$ cfu/ml for the lactobacilli. Cells were incubated at 37° C. and survival measured at intervals of 5, 30, 60 and 120 min using the plate count method.

(b) The *Lactobacillus* strains were propagated in buffered MRS broth (pH 6.0) daily for a 5 day period. The cells were harvested, washed and resuspended in pH adjusted MRS broth and survival measured over a 2 h period using the plate count method.

To determine the ability of the lactobacilli to survive passage through the stomach, an ex-vivo study was performed using human gastric juice. Cells from fresh overnight cultures were harvested, washed twice in buffer (pH 6.5) and resuspended in human gastric juice to a final concentration of $10^6$-$10^8$ cfu/ml, depending on the strain. Survival was monitored over a 30-60 min incubation period at 37° C. The experiment was performed using gastric juice at pH ~1.2 (unadjusted) and pH 2.0 and 2.5.

Each of the *Lactobacillus* strains tested grew normally at pH 6.8 and pH 4.5 reaching stationary phase after 8 h with a doubling time of 80-100 min. At pH 3.5 growth was restricted with doubling times increasing to 6-8 h. No growth was observed at pH 2.5 or lower, therefore, survival of the strains at low pH was examined.

Each of the strains was generally resistant to pH values 3.5, 3.0, and 2.5, with *Lactobacillus salivarius* AH102 and AH105 also exhibiting resistance at pH 2.0 (data not shown).

To determine the ability of the *Lactobacillus* strains to survive conditions encountered in the human stomach, viability of each of the 5 strains was tested in human gastric juice at pH 1.2 and pH 2.5, as shown in Table 6 below. The survival is expressed at log10 cfu/ml (nd=not determined).

TABLE 6

| STRAIN | pH | TIME (min) | | | |
|---|---|---|---|---|---|
| | | 0 | 5 | 30 | 60 |
| *Lactobacillus* sp. | | | | | |
| AH102 | 1.2 | 9.16 | 8.84 | 6.81 | nd |
| | 2.5 | 9.49 | 9.34 | 9.53 | 9.25 |
| AH103 | 1.2 | 9.17 | 8.77 | 3.30 | nd |
| | 2.5 | 9.73 | 9.71 | 9.50 | 9.44 |
| AH105 | 1.2 | 9.38 | 9.00 | 5.87 | nd |
| | 2.5 | 9.69 | 9.49 | 9.62 | 9.51 |
| AH109 | 1.2 | 9.79 | 8.71 | 4.20 | nd |
| | 2.5 | 9.76 | 9.59 | 9.68 | 9.72 |
| AH110 | 1.2 | 9.49 | 8.84 | 6.81 | nd |
| | 2.5 | 9.77 | 9.65 | 9.39 | 9.59 |

Growth of Cultures in the Presence of Bile

Fresh cultures were streaked onto MRS agar plates supplemented with bovine bile (B-8381, Sigma Chemical Co. Ltd., Poole) at concentrations of 0.3, 1.0, 1.5, 5.0 and 7.5% (w/v) and porcine bile (B-863 1, Sigma Chemical Co. Ltd., Poole) at concentrations of 0.3, 0.5, 1.0, 1.5, 5.0 and 7.5% (w/v). Plates were incubated at 37° C. under anaerobic conditions and growth was recorded after 24-48 h.

Bile samples, isolated from several human gall-bladders, were stored at −80° C. before use. For experimental work, bile samples were thawed, pooled and sterilised at 80° C. for 10 min. Bile acid composition of human bile was determined using reverse-phase High Performance Liquid Chromatography (HPLC) in combination with a pulsed amperometric detector according to the method of Dekker et al. (20). Human bile was added to MRS/TPY agar medium at a concentration of 0.3% (v/v). Freshly streaked cultures were examined for growth after 24 and 48 h.

Human gall-bladder bile possesses a bile acid concentration of 50-100 mM and dilution in the small intestine lowers this concentration to 5-10 mM. Furthermore, under physiological conditions, bile acids are found as sodium salts. Therefore, cultures were screened for growth on MRS agar plates containing the sodium salt of each of the following bile acids (Sigma Chemical Co. Ltd., Poole):

(a) conjugated form: taurocholic acid (TCA); glycocholic acid (GCA); taurodeoxycholic acid (TDCA); glycodeoxycholic acid (GDCA); taurochenodeoxycholic acid (TCDCA) and glycochenodeoxycholic acid (GCDCA); (b) deconjugated form: lithocholic acid (LCA); chenodeoxycholic acid (CDCA); deoxycholic acid (DCA) and cholic acid (CA). For each bile acid concentrations of 1, 3 and 5 mM were used. Growth was recorded after 24 and 48 h anaerobic incubation.

Both a qualitative (agar plate) and a quantitative (HPLC) assay were used to determine deconjugation activity.

Plate assay: All the cultures were streaked on MRS agar plates supplemented with (a) 0.3% (w/v) porcine bile, (b) 3 mM TDCA or (c) 3 mM GDCA. Deconjugation was observed as an opaque precipitate surrounding the colonies.

High Performance Liquid Chromatography (HPLC): Analysis of in vitro deconjugation of human bile was performed using HPLC. Briefly, overnight cultures were inoculated (5%) into MRS broth supplemented with 0.3% (v/v) human bile and were incubated anaerobically at 37° C. At various time intervals over a 24 h period, samples (1 ml) were removed and centrifuged at 14,000 rpm for 10 min. Undiluted cell-free supernatant (30 µl) was then analysed by HPLC.

*Lactobacillus salivarius* AH102, AH103, AH105, AH109 and AH110 were capable of growth (bile acid resistance) on three sources of bile used. It was observed that resistance to bovine bile was much higher than to porcine bile. Each of the *Lactobacillus* strains tested was resistant to concentrations up to and including 5.0% bovine bile (data not shown).

Porcine bile was more inhibitory as shown in Table 7 below.

TABLE 7

| STRAIN | % (w/v) PORCINE BILE | | | | | | |
|---|---|---|---|---|---|---|---|
| *Lactobacillus* sp. | 0.0 | 0.3 | 0.5 | 1.0 | 1.5 | 5.0 | 7.5 |
| AH102 | + | + | − | − | − | − | − |
| AH103 | + | + | + | − | − | − | − |
| AH105 | + | + | − | − | − | − | − |
| AH109 | + | + | − | − | − | − | − |
| AH110 | + | + | − | − | − | − | − |

Regardless of the bile resistance profiles in the presence of both bovine and porcine bile, each of the *Lactobacillus salivarius* strains grew to confluence at the physiological concentration of 0.3% (v/v) human bile (data not shown).

Each of the *Lactobacillus* strains, when analysed specifically for its resistance to individual bile acids, grew well in the presence of taurine conjugated bile acids. Isolates from each of Lactobacillus strain grew to confluence on agar medium containing up to and including 5 mM of taurine conjugates TCA, TDCA and TCDCA. Of the glycine conjugates tested, GCDCA was the most inhibitory. GDCA was less inhibitory and GCA was the least inhibitory of the three glycine conjugates. Each of the *Lactobacillus* strains grew on agar medium supplemented with 5 mM GCA. This is shown in Table 8 below.

TABLE 8

| STRAIN | BILE ACIDS (mM) | | | | | | | | | | | |
|---|---|---|---|---|---|---|---|---|---|---|---|---|
| *Lactobacillus* | GCDCA | | | | GDCA | | | | GCA | | | |
| sp. | 0 | 1 | 3 | 5 | 0 | 1 | 3 | 5 | 0 | 1 | 3 | 5 |
| AH102 | + | + | − | − | + | + | − | − | + | + | + | + |
| AH103 | + | + | − | − | + | + | − | − | + | + | + | + |
| AH105 | + | + | − | − | + | + | + | − | + | + | + | + |
| AH109 | + | + | − | − | + | + | − | − | + | + | + | + |
| AH110 | + | + | − | − | + | + | − | − | + | + | + | + |

−; no growth;
+; confluent growth

Growth in the presence of deconjugated bile acids was also tested. Each *Lactobacillus* strain was resistant to concentrations of 5 mM LCA. Growth in the presence of CA was also tested. As shown in Table 9 below, three of the 5 strains, AH102, AH105 and AH109 grew in the presence of 1 mM CA. None of the strains grew in the presence of 1 mM CDCA. (data not shown).

TABLE 9

| STRAIN | CHOLIC ACID (mM) | | | |
|---|---|---|---|---|
| Lactobacillus sp. | 0 | 1 | 3 | 5 |
| AH102 | + | + | − | − |
| AH103 | + | − | − | − |
| AH105 | + | + | − | − |
| AH109 | + | + | − | − |
| AH110 | + | − | − | − |

Detection of Antimicrobial Activity

Antimicrobial activity was detected using the deferred method (21). Indicators used in the initial screening were *L. innocua, L. fermentum* KLD, *P. flourescens* and *E. coli* V157. Briefly, the lactobacilli (MRS) were incubated for 12-16 h and 36-48 h, respectively. Ten-fold serial dilutions were spread-plated (100 µl) onto MRS/TPY agar medium. After overnight incubation, plates with distinct colonies were overlayed with the indicator bacterium. The indicator lawn was prepared by inoculating a molten overlay with 2% (v/v) of an overnight indicator culture which was poured over the surface of the inoculated MRS plates. The plates were re-incubated overnight under conditions suitable for growth of the indicator bacterium. Indicator cultures with inhibition zones greater than 1 mm in radius were considered sensitive to the test bacterium.

Inhibition due to bacteriophage activity was excluded by flipping the inoculated MRS/TPY agar plates upside down and overlaying with the indicator. Bacteriophage cannot diffuse through agar.

*Lactobacillus salivarius* AH102, AH103, AH105, AH109 and AH110 were screened for inhibitory activity using *Ls. innocua, L. fermentum* KLD, *P. fluorescens* and *E. coli* as indicator microorganisms. When the test strains were inoculated on unbuffered MRS, inhibition of the four indicators was observed. Zones ranging in size from 1 mm to 5 mm were measured. Inhibition of *Ls. innocua* by each of the lactobacilli produced the largest zones.

EXAMPLE 2

Adhesion of Probiotic Bacteria to Gastrointestinal Epithelial Cells

Adhesion Assay

The adhesion of the probiotic strains was carried out using a modified version of a previously described method (22). The monolayers of HT-29 and Caco-2 cells were prepared on sterile 22 mm$^2$ glass coverslips, which were placed in Corning tissue culture dishes, at a concentration of $4 \times 10^4$ cells/ml.° Cells were fed fresh medium every 2 days. After ~10 days, and differentiation of the monolayer had occurred, the monolayers were washed twice with Phosphate Buffered Saline (PBS). Antibiotic-free DMEM (2 ml) and 2 ml of 18 h Lb. suspension containing ~$10^9$ cfu/ml were added to each dish and cells were incubated for 2 h at 37° C. in a humidified atmosphere containing 5% $CO_2$. After incubation, the monolayers were washed 5 times with PBS, fixed in methanol (BDH Laboratory Supplies, Poole, UK) for 3 min, Gram stained (Gram Stain Set, Merck) and examined microscopically under oil immersion. For each glass coverslip monolayer the number of adherent bacteria per 20 epithelial cells was counted in 10 microscopic fields. The mean and standard error of adherent bacteria per 20 epithelial cells was calculated. Each adhesion assay was carried out in duplicate.

In a second method, after washing 5 times in PBS, adhering bacteria were removed by vortexing the monolayers rigorously in cold sterile $H_2O$. Bacterial cells were enumerated by serial dilution in quarter strength Ringer's solution (Oxoid) and incubation on MRS (Lactobacilli).

Figure 1:
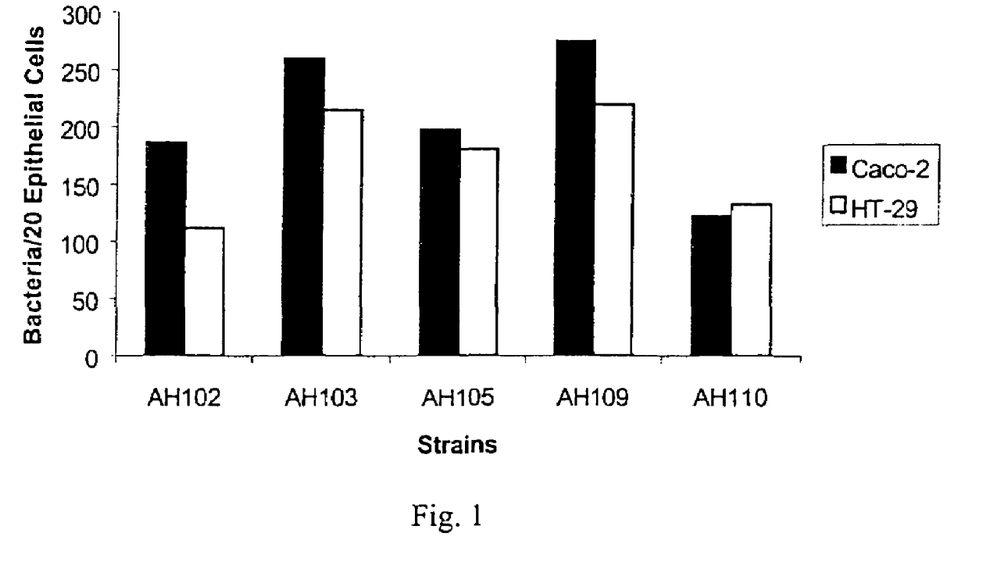
FIG. 1 is a bar graph showing the number of adherent bacteria per 20 epithelial cells using human gastrointestinal epithelial cells, CaCo-2 and HT-29.

Each of the 5 *Lactobacillus* strains, AH102, AH103, AH105, AH109 and AH110 adhered to gastrointestinal epithelial cells (FIG. 1). These probiotic strains would be suitable as vaccine/drug delivery vehicles as they adhere to the gastrointestinal epithelium and therefore interact with the relevant host tissue.

EXAMPLE 3

Determination of the Effect of each of the *Lactobacillus* Strains on PBMC Cytokine Production Peripheral blood mononuclear cells were isolated from healthy donors (n=19) by density gradient centrifugation. PBMCs were stimulated with the probiotic bacterial strains for a 72 hour period at 37° C. At this time culture supernatants were collected, centrifuged, aliquoted and stored at −70° C. until being assessed for IL-8, IL-10, IL-12 and IFNγ levels using ELISAs (Boehringer Mannheim).

Figure 2:
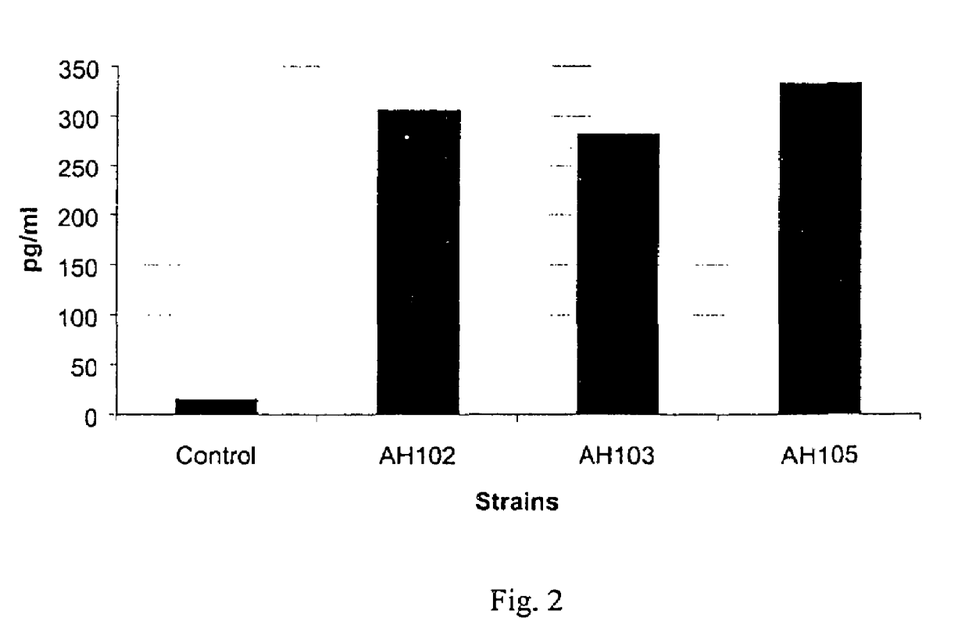
FIG. 2 is a bar graph showing IFNγ levels induced by PBMCs following co-incubation with *Lactobacillus salivarius* strains.

AH102, AH103 and AH105 stimulated production of IFNγ from PBMCs (FIG. 2).

Figure 3:
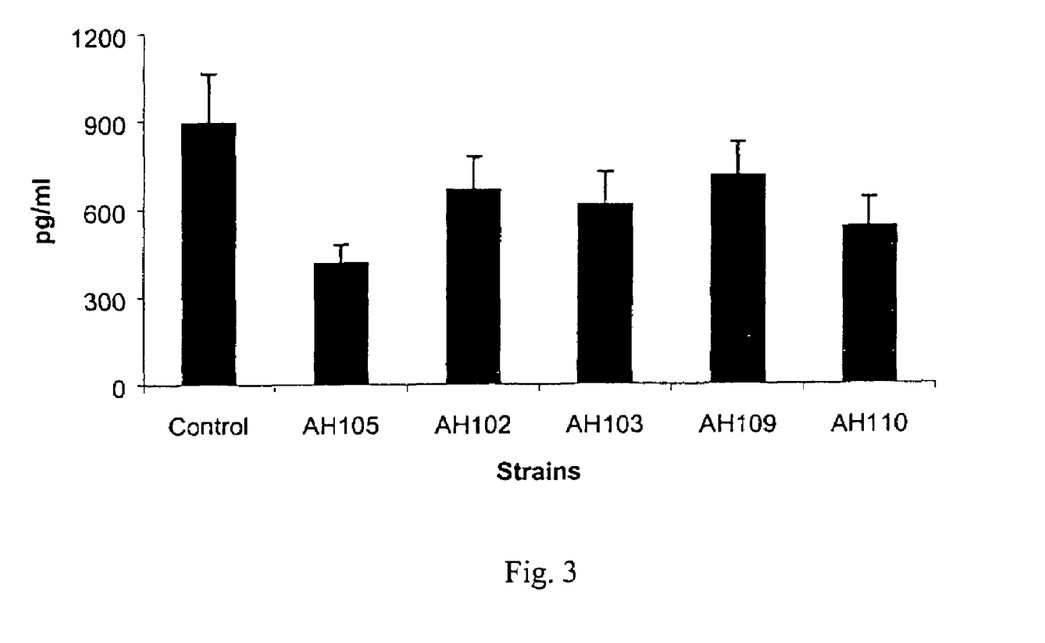
FIG. 3 is a bar graph showing the effect on the levels of IL-10 (pg/ml) induced by PBMCs following co-incubation with *Lactobacillus salivarius* strains.

AH102, AH103, AH109 and AH110 co-incubation did not significantly alter IL-10 levels (FIG. 3). Stimulation with AH105 significantly reduced secretion. of IL-10 by PBMCs.

Figure 4:
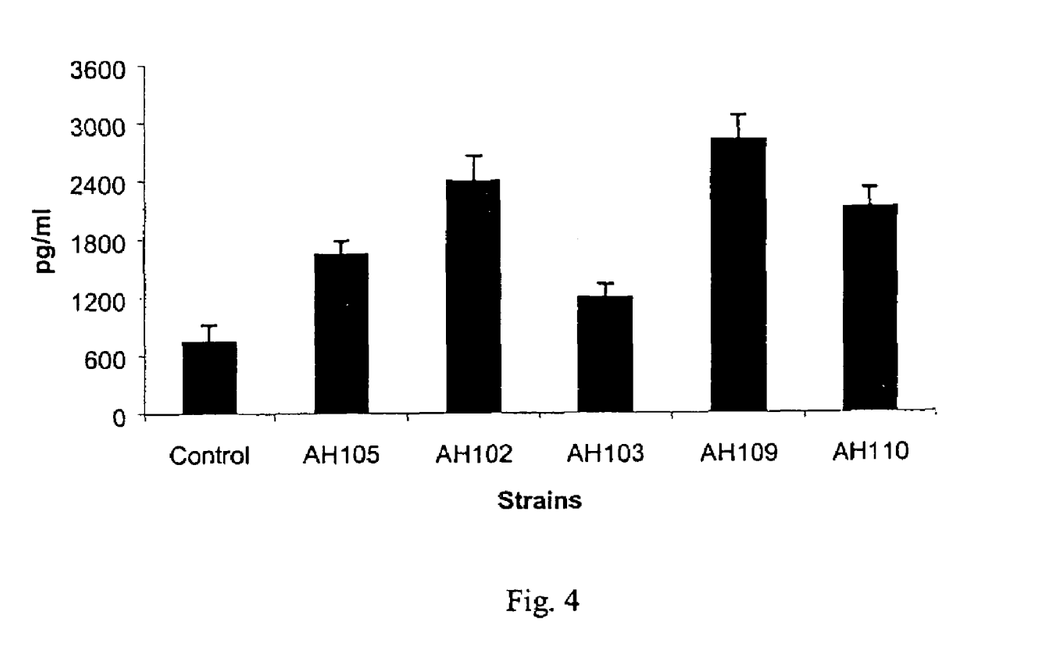
FIG. 4 is a bar graph showing the effect of *Lactobacillus salivarius* strains on PBMC IL-12 (pg/ml) production.

AH102, AH105, AH109 and AH110 co-incubation significantly upregulated IL-12 production by PBMCs (FIG. 4). AH103 had no significant effect on IL-12 production.

Figure 5:
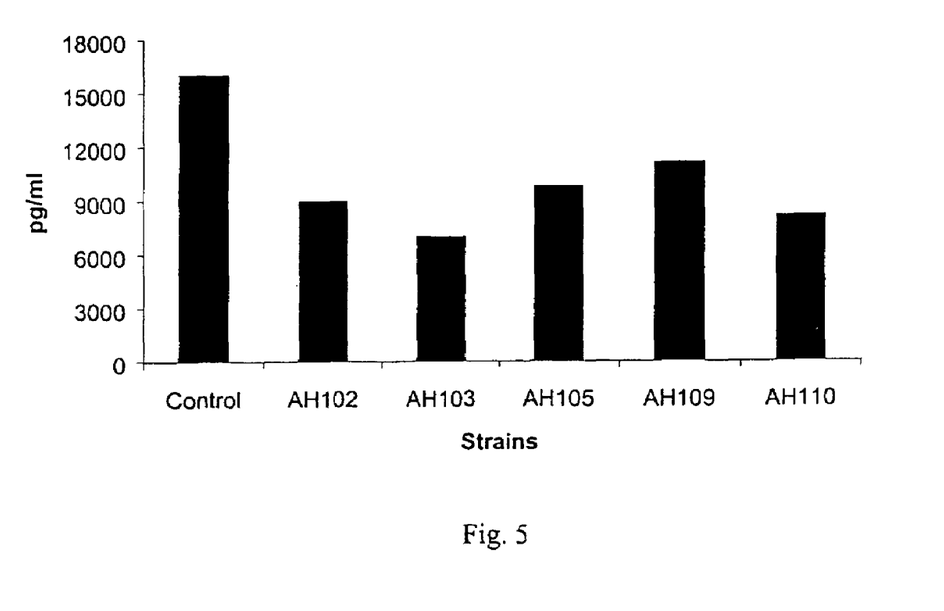
FIG. 5 is a bar graph showing the effect of *Lactobacillus salivarius* strains on PBMC IL-8 (pg/ml) production.

None of the 5 *Lactobacillus* strains stimulated IL-8 production in vitro, from PBMCs isolated from healthy donors. Indeed, in each case, IL-8 levels were reduced (FIG. 5).

EXAMPLE 4

Determination of Cytokine Levels in an Epithelial/PBMC Co-Culture Model following Incubation with AH103 and AH110

The appropriate in vitro model with physiological relevance to the intestinal tract is a culture system incorporating epithelial cells, T cells, B cells, monocytes and the bacterial strains. To this end, human Caco-2 epithelial cells were seeded at $5 \times 10^5$ cells/ml on the apical surface of 25 mm transwell inserts with a pore size of 3 □m (Costar). These cells were cultured for four weeks in RPMI 1640, supplemented with 10% foetal calf serum, glutamine, penicillin and streptomycin, at 37° C. in a 5% $CO_2$ environment. Culture media was changed every 3 days. When the epithelial cells were fully differentiated, human peripheral blood mononuclear cells (PBMCs) were isolated by density gradient centrifugation. $1 \times 10^6$ washed PBMCs was incubated basolaterally to the epithelial cells and cultured with $1 \times 10^7$ probiotic bacteria. Controls contained media alone. No direct cell-cell contact between PBMCs and epithelial cells was possible in this model system and cellular communication was mediated solely by soluble factors.

Following 72 hours of incubation with AH103 or AH110, cell culture supernatants were removed, aliquoted and stored at −70° C. TNFα and IL-8 extracellular cytokine levels were measured using standard ELISA kits (R&D. Systems). TNFα levels and IL-8 levels were measured, in duplicate, using PBMCs from 3 healthy volunteers.

Figure 6:
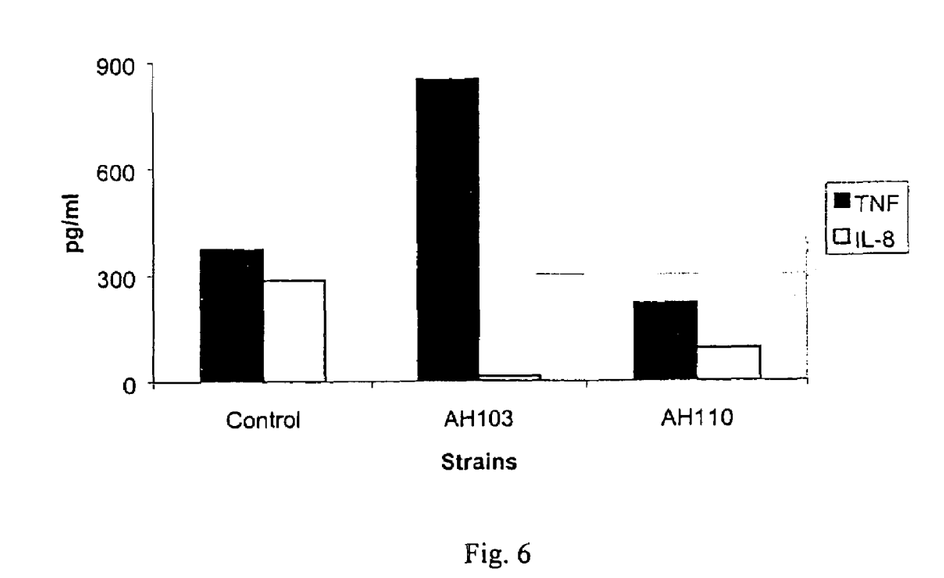
FIG. 6 is a bar graph showing the ability of *Lactobacillus salivarius* strains to modulate proinflammatory cytokine production measured in pg/ml.

Following incubation of epithelial cell-PBMC co-cultures with probiotic bacteria, TNFα and IL-8 cytokine levels were examined by ELISAs (FIG. 6). AH103 significantly reduced the level of IL-8 released by these cells. AH110 reduced the levels of TNFα and IL-8 released by these cells.

Immunomodulation

The human immune system plays a significant role in the aetiology and pathology of a vast range of human diseases. Hyper and hypo-immune responsiveness results in, or is a component of, the majority of disease states. One family of biological entities, termed cytokines, are particularly important to the control of immune processes. Pertubances of these delicate cytokine networks are being increasingly associated with many diseases. These diseases include but are not limited to inflammatory disorders, immunodeficiency, inflammatory bowel disease, irritable bowel syndrome, cancer (particularly those of the gastrointestinal and immune systems), diarrhoeal disease, antibiotic associated diarrhoea, paediatric diarrhoea, appendicitis, autoimmune disorders, multiple sclerosis, Alzheimer's disease, rheumatoid arthritis, coeliac disease, diabetes mellitus, organ transplantation, bacterial infections, viral infections, fungal infections, periodontal disease, urogenital disease, sexually transmitted disease, HIV infection, HIV replication, HIV associated diarrhoea, surgical associated trauma, surgical-induced metastatic disease, sepsis, weight loss, anorexia, fever control, cachexia, wound healing, ulcers, gut barrier function, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, epidermal disorders, psoriasis and acne vulgaris. The effects on cytokine production are specific for each of the probiotic strains examined. Thus specific probiotic strains may be selected for normalising an exclusive cytokine imbalance particular for a specific disease type. Customisation of disease specific therapies can be accomplished using a selection of the probiotic strains listed above.

Immune Education

The enteric flora is important to the development and proper function of the intestinal immune system. In the absence of an enteric flora, the intestinal immune system is underdeveloped, as demonstrated in germ free animal models, and certain functional parameters are diminished, such as macrophage phagocytic ability and immunoglobulin production (23). The importance of the gut flora in stimulating non-damaging immune responses is becoming more evident. The increase in incidence and severity of allergies in the western world has been linked with an increase in hygiene and sanitation, concomitant with a decrease in the number and range of infectious challenges encountered by the host. This lack of immune stimulation may allow the host to react to non-pathogenic, but antigenic, agents resulting in allergy or autoimmunity. Deliberate consumption of a series of non-pathogenic immunomodulatory bacteria would provide the host with the necessary and appropriate educational stimuli for proper development and control of immune function.

Inflammation

Inflammation is the term used to describe the local accumulation of fluid, plasma proteins and white blood cells at a site that has sustained physical damage, infection or where there is an ongoing immune response. Control of the inflammatory response is exerted on a number of levels (24). The controlling factors include cytokines, hormones (e.g. hydrocortisone), prostaglandins, reactive intermediates and leukotrienes. Cytokines are low molecular weight biologically active proteins that are involved in the generation and control of immunological and inflammatory responses, while also regulating development, tissue repair and haematopoiesis. They provide a means of communication between leukocytes themselves and also with other cell types. Most cytokines are pleiotrophic and express multiple biologically overlapping activities. Cytokine cascades and networks control the inflammatory response rather than the action of a particular cytokine on a particular cell type (25). Waning of the inflammatory response results in lower concentrations of the appropriate activating signals and other inflammatory mediators leading to the cessation of the inflammatory response. TNFα is a pivotal proinflammatory cytokine as it initiates a cascade of cytokines and biological effects resulting in the inflammatory state. Therefore, agents which inhibit TNFα are currently being used for the treatment of inflammatory diseases, e.g. infliximab.

Pro-inflammatory cytokines are thought to play a major role in the pathogenesis of many inflammatory diseases, including inflammatory bowel disease (IBD). Current therapies for treating IBD are aimed at reducing the levels of these pro-inflammatory cytokines, including IL-8 and TNFα. Such therapies may also play a significant role in the treatment of systemic inflammatory diseases such as rheumatoid arthritis.

Irritable bowel syndrome (IBS) is a common gastrointestinal disorder, affecting up to 15-20% of the population at some stage during their life. The most frequent symptoms include abdominal pain, bowel habit disturbance, manifested by diarrhoea or constipation, flatulence, and abdominal distension. There are no simple tests to confirm diagnosis, and if no other organic disorders can be found for these symptoms, the diagnosis is usually IBS. Patients suffering from IBS represent as many as 25-50% of patients seen by gastroenterologists.

Many factors are thought to be involved in onset of symptoms including e.g. bout of gastroenteritis, abdominal or pelvic surgery, disturbances in the intestinal bacterial flora, perhaps due to antibiotic intake, and emotional stress. Compared with the general population, IBS sufferers may have a significantly reduced quality of life, are more likely to be absent from work, and use more healthcare resources. There are no effective medical treatments and to date, recommended therapies have included antispasmodic agents, anti-diarrhoeal agents, dietary fibre supplements, drugs that modify the threshold of colonic visceral perception, analgesics and antidepressants.

While each of the strains of the invention have unique properties with regard to cytokine modulation and microbial antagonism profiles, it should be expected that specific strains can be chosen for use in specific disease states based on these properties. It also should be anticipated that combinations of strains from this panel with appropriate cytokine modulating properties and anti-microbial properties will enhance therapeutic efficacy.

The strains of the present invention may have potential application in the treatment of a range of inflammatory diseases, particularly if used in combination with other anti-inflammatory therapies, such as non-steroid anti-inflammatory drugs (NSAIDs) or Infliximab.

Cytokines and Cancer

The production of multifunctional cytokines across a wide spectrum of tumour types suggests that significant inflammatory responses are ongoing in patients with cancer. It is currently unclear what protective effect this response has against the growth and development of tumour cells in vivo. However, these inflammatory responses could adversely affect the tumour-bearing host. Complex cytokine interactions are involved in the regulation of cytokine production and cell proliferation Within tumour and normal tissues (26, 27). It has long been recognized that weight loss (cachexia) is the single most common cause of death in patients with cancer and initial malnutrition indicates a poor prognosis. For a tumour to grow and spread it must induce the formation of new blood vessels and degrade the extracellular matrix. The inflammatory response may have significant roles to play in the above mechanisms, thus contributing to the decline of the host and progression of the tumour. Due to the anti-inflammatory properties of *Lactobacillus salivarius* these bacterial strains they may reduce the rate of malignant cell transformation. Furthermore, intestinal bacteria can produce, from dietary compounds, substances with genotoxic, carcinogenic and tumour-promoting activity and gut bacteria can activate pro-carcinogens to DNA reactive agents (28). In general, species of *Lactohacillus* have low activities of xenobiotic metabolizing enzymes compared to other populations within the gut such as bacteroides, eubacteria and clostridia. Therefore, increasing the number of *Lactobacillus* bacteria in the gut could beneficially modify the levels of these enzymes.

Vaccine/Drug Delivery

The majority of pathogenic organisms gain entry via mucosal surfaces. Efficient vaccination of these sites protects against invasion by a particular infectious agent. Oral vaccination strategies have concentrated, to date, on the use of attenuated live pathogenic organisms or purified encapsulated antigens (29). Probiotic bacteria, engineered to produce antigens from an infectious agent, in vivo, may provide an attractive alternative as these bacteria are considered to be safe for human consumption (GRAS status).

Murine studies have demonstrated that consumption of probiotic bacteria expressing foreign antigens can elicit protective immune responses. The gene encoding tetanus toxin fragment C (TTFC) was expressed in *Lactococcus lactis* and mice were immunized via the oral route. This system was able to induce antibody titers significantly high enough to protect the mice from lethal toxin challenge. In addition to antigen presentation, live bacterial vectors can produce bioactive compounds, such as immunostimulatory cytokines, in vivo. *L. lactis* secreting bioactive human IL-2 or IL-6 and TTFC induced 10-15 fold higher serum IgG titres in mice immunized intranasally (30). However, with this particular bacterial strain, the total IgA level was not increased by coexpression with these cytokines. Other bacterial strains, such as *Streptococcus gordonii*, are. also being examined for their usefulness as mucosal vaccines. Recombinant *S. gordonii* colonizing the murine oral and vaginal cavities induced both mucosal and systemic antibody responses to antigens expressed by this bacterial (31). Thus oral immunization using probiotic bacteria as vectors would not only protect the host from infection, but may replace the immunological stimuli that the pathogen would normally elicit thus contributing to the immunological education of the host.

Prebiotics

The introduction of probiotic organisms is accomplished by the ingestion of the micro-organism in a suitable carrier. It would be advantageous to provide a medium that would promote the growth of these probiotic strains in the large bowel. The addition of one or more oligosaccharides, polysaccharides, or other prebiotics enhances the growth of lactic acid bacteria in the gastrointestinal tract. Prebiotics refers to any non-viable food component that is specifically fermented in the colon by indigenous bacteria thought to be of positive value, e.g. bifidobacteria, lactobacilli. Types of prebiotics may include those that contain fructose, xylose, soya, galactose, glucose and mannose. The combined administration of a probiotic strain with one or more prebiotic compounds may enhance the growth of the administered probiotic in vivo resulting in a more pronounced health benefit, and is termed synbiotic.

Other Active Ingredients

It will be appreciated that the probiotic strains may be administered prophylactically or as a method of treatment either on its own or with other probiotic and/or prebiotic materials as described above. In addition, the bacteria may be used as part of a prophylactic or treatment regime using other active materials such as those used for treating inflammation or other disorders especially those with an immunological involvement. Such combinations may be administered in a single formulation or as separate formulations administered at the same or different times and using the same or different routes of administration.

The invention is not limited to the embodiments herein before described which may be varied in detail.

REFERENCES

1. McCracken V. J. and Gaskins H. R. Probiotics and the immune system. In: *Probiotics a critical review*, Tannock, G W (ed), Horizon Scientific Press, UK. 1999, p. 85-113.
2. Savage D. C. Interaction between the host and its microbes. In: *Microbial Ecology of the Gut*, Clark and Bauchop (eds), Academic Press, London. 1977, p. 277-310.
3. Kagnoff M. F. Immunology of the intestinal tract. *Gastroenterol.* 1993; 105 (5): 1275-80.
4. Lamm M. E. Interaction of antigens and antibodies at mucosal surfaces. *Ann. Rev. Microbiol.* 1997; 51: 311-40.
5. Raychaudhuri S., Rock K L. Fully mobilizing host defense: building better vaccines. *Nat biotechnol.*, 1998; 16: 1025-31.
6. Stallmach A., Strober W, MacDonald T T, Lochs H, Zeitz M. Induction and modulation of gastrointestinal inflammation. *Immunol. Today,* 1998; 19 (10): 438-41.
7. de Waal Malefyt R, Haanen J, Spits H, Roncarolo M G, te Velde A, Figdor C, Johnson K, Kastelein R, Yssel H, de Vries JE. Interleukin 10 (IL-10) and viral IL-10 strongly reduce antigen-specific human T cell proliferation by diminishing the antigen-presenting capacity of monocytes via downregulation of class II major histocompatibility complex expression. J Exp Med 1991 October 1;174(4): 915-24.
8. Schmitt E, Rude E, Germann T. The immunostimulatory function of IL-12 in T-helper cell development and its regulation by TGF-beta, IFN-gamma and IL-4. Chem Immunol 1997;68:70-85.
9. Leonard J P, Waldburger K E, Schaub R G, Smith T, Hewson A K, Cuzner M L, Goldman S J. Regulation of the inflammatory response in animal models of multiple sclerosis by interleukin-12. Crit Rev Immunol 1997; 17(5-6): 545-53.
10. Donnelly R P, Fenton M J, Finbloom D S, Gerrard T L. Differential regulation of IL—production in human monocytes by IFN-gamma and IL-4. *J Immunol* 1990 Jul. 15; 145(2):569-75.
11. Wahl S M, Allen J B, Ohura K, Chenoweth D E, Hand A R, IFN-gamma inhibits inflammatory cell recruitment and the evolution of bacterial; cell wall-induced arthritis. *J Immunol* 1991 Jan. 1;146(1):95-100.

12. Gatanaga T, Hwang C D, Kohr W, Cappuccini F, Lucci J A 3d, Jeffes E W, Lentz R, Tomich J, Yamamoto R S, Granger G A. Purification and characterization of an inhibitor (soluble tumor necrosis factor receptor) for tumor necrosis factor and lymphotoxin obtained from the serum ultrafiltrates of human cancer patients. *Proc Natl Acad Sci U S A* 1990 November;87(22):8781-4.
13. Kawakami M, Ihara I, Ihara S, Suzuki A, Fukui K. A group of bactericidal factors conserved by vertebrates for more than 300 million years. *J Immunol* 1984 May; 132(5): 2578-81.
14. Mestan J, Digel W, Mittnacht S, Hillen H, Blohm D, Moller A, Jacobsen H, Kirchner H. Antiviral effects of recombinant tumour necrosis factor in vitro. *Nature* 1986 Oct. 30-Nov. 5;323(6091):816-9.
15. Ferrante A, Nandoskar M, Walz A, Goh D H, Kowanko I C. Effects of tumour necrosis factor alpha and interleukin-1 alpha and beta on human neutrophil migration, respiratory burst and degranulation. *Int Arch Allergy Appl Immunol* 1988;86(1):82-91.
16. Bachwich P R, Chensue S W, Larrick J W, Kunkel S L. Tumor necrosis factor stimulates interleukin-1 and prostaglandin E2 production in resting macrophages. *Biochem Biophys Res Commun* 1986 Apr. 14; 136(1):94-101.
17. Cicco N A, Lindemann A, Content J, Vandenbussche P, Lubbert M, Gauss J, Mertelsmann R, Herrmann F. Inducible production of interleukin-6 by human polymorphonuclear neutrophils: role of granulocyte-macrophage colony-stimulating factor and tumor necrosis factor-alpha. *Blood* 1990 May 15;75(10):2049-52.
18. Mangan D F, Welch G R, Wahl S M. Lipopolysaccharide, tumor necrosis factor-alpha, and IL-1 beta prevent programmed cell death (apoptosis) in human peripheral blood monocytes. *J Immunol* 1991 Mar. 1;146(5):1541-6.
19. Dinarello C A, Cannon J G, Wolff S M. New concepts on the pathogenesis of fever. *Rev Infect Dis* 1988 January-February;10(1): 168-89.
20. Dekker, R, van der Meer, R, Olieman, C. Sensitive pulsed amperometric detection of free and conjugated bile acids in combination with gradient reversed-phase HPLC. *Chromatographia* 1991; 31(11/12): 549-553.
21. Tagg, J R, Dajani, A S, Wannamaker, L W. Bacteriocins of Gram positive bacteria. *Bacteriol Rev.* 1976; 40: 722-756.
22. Chauviere, G., M. H. Cocconier, S. Kerneis, J. Foumiat and A. L. Servin. Adherence of human *Lactobacillus acidophilus* strains LB to human enterocyte-like Caco-2 cells. *J. Gen. Microbiol.* 1992; 138: 1689-1696
23. Crabbe P. A., H. Bazin, H. Eyssen, and J. F. Heremans. The normal microbial flora as a major stimulus for. proliferation of plasma cells synthesizing IgA in the gut. The germ free intestinal tract. *Into. Arch. Allergy Appl Immunol,* 1968; 34: 362-75.
24. Henderson B., Poole, S and Wilson M. 1998. In "Bacteria-Cytokine interactions in health and disease. Portland Press, 79-130.
25. Arai K I, Lee F, Miyajima A, Miyatake S, Arai N, Yokota T. Cytokines: coordinators of immune and inflammatory responses. *Annu Rev Biochem* 1990;59:783-836.
26. McGee D W, Bamberg T, Vitkus S J, McGhee J R. A synergistic relationship between TNF-alpha, IL-1 beta, and TGF-beta 1 on IL-6 secretion by the IEC-6 intestinal epithelial cell line. *Immunology* 1995 September;86(1):6-11.
27. Wu S, Meeker W A, Wiener J R, Berchuck A, Bast R C Jr, Boyer C M. Transfection of ovarian cancer cells with tumour necrosis factor alpha (TNF-alpha) antisense mRNA abolishes the proliferative response to interleukin-1 (IL-1) but not TNF-alpha. *Gynecol Oncol* 1994 April; 53(1):59-63.
28. Rowland I. R. Toxicology of the colon: role of the intestinal microflora. In: Gibson G. R. (ed). *Human colonic bacteria: role in nutrition, physiology and pathology,* 1995, pp 155-174. Boca Raton CRC Press.
29. Walker, R. I. New strategies for using mucosal vaccination to achieve more effective immunization. *Vaccine,* 1994; 12: 387-400.
30. Steidler L., K. Robinson, L. Chamberlain, K. M Scholfield, E. Remaut, R. W. F. Le Page and J. M. Wells. Mucosal delivery of murine interleukin-2 (IL-2) and IL-6 by recombinant strains of Lactococcus lactis coexpressing antigen and cytokine. *Infect. Immun.,* 1998; 66:3183-9.
31. Medaglini D., G. Pozzi, T. P. King and V. A. Fischetti. Mucosal and systemic immune responses to a recombinant protein expressed on the surface of the oral commensal bacterium *Streptococcus gordonii* after oral colonization. *Proc. Natl. Acad. Sci. USA,* 1995;92:6868-72.

The invention claimed is:

1. An isolated strain of *Lactobacillus salivarius* NCIMB 41044.
2. An isolated strain of *Lactobacillus salivarius* NCIMB 41045.
3. An isolated strain of *Lactobacillus salivarius* NCIMB 41093.
4. An isolated strain of *Lactobacillus salivarius* NCIMB 41094.
5. The strain of claim 1 in the form of viable cells.
6. The strain of claim 1 in the form of non-viable cells.
7. The strain of claim 2 in the form of viable cells.
8. The strain of claim 2 in the form of non-viable cells.
9. The strain of claim 3 in the form of viable cells.
10. The strain of claim 3 in the form of non-viable cells.
11. The strain of claim 4 in the form of viable cells.
12. The strain of claim 4 in the form of non-viable cells.
13. A food stuff comprising the strain of *Lactobacillus salivarius* of claim 1.
14. A food stuff comprising the strain of *Lactobacillus salivarius* of claim 2.
15. A food stuff comprising the strain of *Lactobacillus salivarius* of claim 3.
16. A food stuff comprising the strain of *Lactobacillus salivarius* of claim 4.
17. A pharmaceutical composition comprising the *Lactobacillus salivarius* strain of claim 1 and a pharmaceutically acceptable carrier.
18. A pharmaceutical composition comprising the *Lactobacillus salivarius* strain of claim 2 and a pharmaceutically acceptable carrier.
19. A pharmaceutical composition comprising the *Lactobacillus salivarius* strain of claim 3 and a pharmaceutically acceptable carrier.
20. A pharmaceutical composition comprising the *Lactobacillus salivarius* strain of claim 4 and a pharmaceutically acceptable carrier.

* * * * *